United States Patent
Moore

(10) Patent No.: US 7,408,632 B2
(45) Date of Patent: Aug. 5, 2008

(54) MISCIBILITY DETERMINATION OF A COMBINATION OF LIQUIDS

(75) Inventor: Christopher B. Moore, Cambridge, MA (US)

(73) Assignee: TransForm Pharmaceuticals, Inc., Lexington, MA (US)

(*) Notice: Subject to any disclaimer, the term of this patent is extended or adjusted under 35 U.S.C. 154(b) by 363 days.

(21) Appl. No.: 11/060,180

(22) Filed: Feb. 17, 2005

(65) Prior Publication Data

US 2005/0185184 A1 Aug. 25, 2005

Related U.S. Application Data

(60) Provisional application No. 60/546,585, filed on Feb. 20, 2004, provisional application No. 60/612,850, filed on Sep. 24, 2004.

(51) Int. Cl.
*G01N 21/41* (2006.01)
(52) U.S. Cl. .................................................. 356/134
(58) Field of Classification Search ................. 356/134, 356/432–436, 428
See application file for complete search history.

(56) References Cited

U.S. PATENT DOCUMENTS

| | | | | |
|---|---|---|---|---|
| 4,436,420 A | * | 3/1984 | Depp et al. ................. | 356/128 |
| 4,569,590 A | * | 2/1986 | Karny et al. ................ | 356/128 |
| 4,679,936 A | * | 7/1987 | Gerharz ...................... | 356/128 |
| 4,710,643 A | * | 12/1987 | Schmukler et al. .......... | 250/573 |
| 5,422,714 A | * | 6/1995 | Fladd .......................... | 356/128 |
| 5,463,228 A | * | 10/1995 | Krause ....................... | 250/577 |
| 6,356,675 B1 | | 3/2002 | Weiss | |

FOREIGN PATENT DOCUMENTS

WO 2004/053468 6/2004

OTHER PUBLICATIONS

Chhaniwal, Vani K., "New optical techniques for diffusion studies in transparent liquid solutions", J. Opt. A: Pure Appl. Opt. vol. 5. pp. A329-337, (Aug. 22, 2003).*
Alanis, Elvio E., "Interferometric measurement of diffusion coefficients through a scanning laser beam", Opt. Eng 39(3), pp. 744-750, (Mar. 2000).*
Spagnolo, Giuseppe Schirripa, "Diffractive optical element based sensor to measure small diffusion coefficients", Proceedings of SPIE vol. 5191. pp. 244-254, (Nov. 2003).*
Dalziel, S.B., "Whole-field density measurements by 'synthetic schlieren'", Experiments in Fluids, vol. 28, pp. 322-335, (2000).*

* cited by examiner

*Primary Examiner*—Tarifur Chowdhury
*Assistant Examiner*—Jonathan M Hansen
(74) *Attorney, Agent, or Firm*—M. Andrea Ryan

(57) ABSTRACT

The present invention provides methods for the determination of miscibility of a mixture of two or more liquids. Measurements of the local deviation of a pattern characteristic or of the variation in light intensity are employed in such determinations.

9 Claims, 1 Drawing Sheet

MISCIBILITY DETERMINATION OF A COMBINATION OF LIQUIDS

CROSS-REFERENCE TO RELATED APPLICATIONS

The present application claims the benefit of priority of U.S. Provisional Application Ser. No. 60/546,585, filed Feb. 20, 2004, and U.S. Provisional Application Ser. No. 60/612,850, filed Sep. 24, 2004, the contents of which are incorporated herein by reference in their entirety.

FIELD OF THE INVENTION

The present invention comprises methods for the determination of miscibility of a mixture of two or more liquids. Electromagnetic radiation can be used to interrogate liquid mixtures of any combination and any ratio in the determination of miscibility.

SUMMARY OF THE INVENTION

In one aspect, the present invention provides methods for the determination of miscibility of a mixture of two or more liquids comprising:

preparing the mixture in a container;
(a) placing the container in proximity to a reference pattern;
(b) irradiating the mixture; and
(c) measuring any local deviation of a pattern characteristic of the reference pattern.

In one embodiment, the container is placed behind the reference pattern with respect to the source of irradiation. In another embodiment, the container is placed in front of the reference pattern with respect to the source of irradiation.

In another embodiment, the reference pattern is substantially transparent. In another embodiment, the reference pattern is opaque. In another embodiment, the reference pattern is reflective.

In another embodiment, the mixture is irradiated at multiple positions between the top and bottom of the liquid in the container. In another embodiment, the mixture contains at least two liquid phases. In another embodiment, the local deviation is measured in each liquid phase. In another embodiment, the local deviation is measured following transmission of radiation through, first, the container, followed by the reference pattern. In another embodiment, the local deviation is measured following transmission of radiation through, first, the reference pattern, followed by the container.

In another embodiment, the local deviation is measured using a photodetector. In another embodiment, the photodetector is positioned in front of the container and the reference pattern. In another embodiment, the photodetector is positioned behind the container and the reference pattern. In another embodiment, the photodetector is positioned at an angle suitable to detect transmitted or reflected radiation from the container and the reference pattern. In another embodiment, the local deviation is measured using a CCD camera.

In another embodiment, a method for the determination of miscibility of a mixture of two or more liquids is provided, comprising:
(a) preparing the mixture in a container;
(b) placing the container between a laser source and a photodetector;
(c) scanning the mixture in a vertical direction; and
(d) measuring any variation in beam intensity.

DETAILED DESCRIPTION OF THE INVENTION

Figure 1:
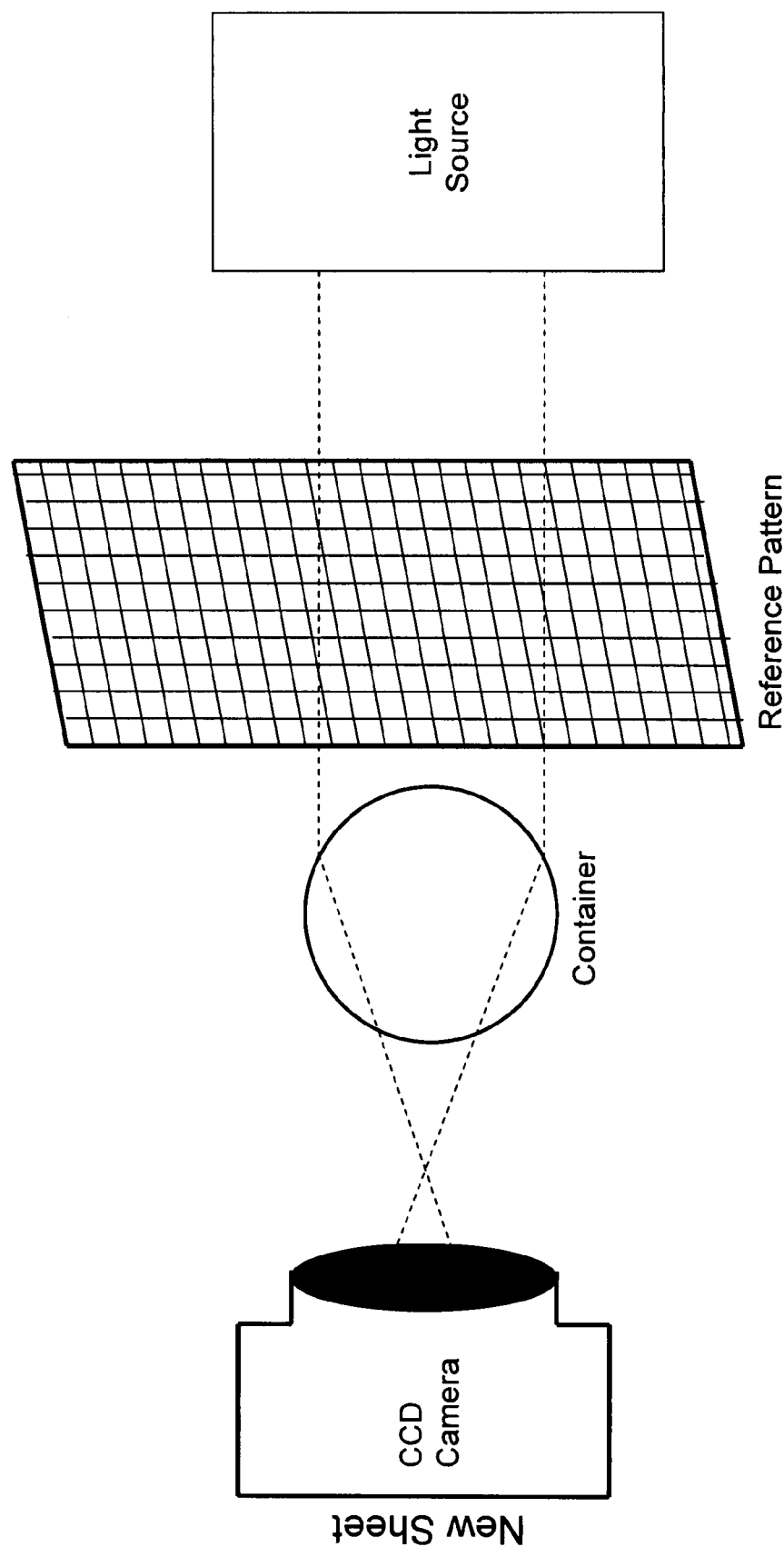
FIG. 1 shows a top view of one embodiment of the present invention including a light source, a reference pattern, a container, and a CCD camera.

Liquid formulations of compounds (e.g., pharmaceuticals and agrochemicals) commonly comprise two or more liquids to solubilize the active ingredient and enable the formulation to provide the desired effect. The search for the optimum mixture of liquid excipients for a particular active ingredient is hindered by the unpredictable nature of miscibility. The ability of two or more liquid components to mix or dissolve in each other in all proportions is known as miscibility. The miscibility of a combination of liquids depends on the nature of the liquid components used (i.e., chemical composition).

In technical fields relating to chemical formulation of compounds such as, but not limited to, the fields of pharmaceutical and agrochemical research and development, it is frequently necessary to evaluate the general suitability of a newly developed liquid formulation candidate prior to launching into full development. Such an evaluation of the general suitability or, in the field of pharmaceutical development, therapeutic effectiveness of such a formulation should typically include miscibility studies of the component excipients.

The compatibility of various solvents and excipients should be tested under a variety of conditions (i.e., temperature, humidity) in order to determine which combinations will remain homogeneous upon storage of a particular liquid formulation. This can be completed, for example, by a combinatorial screen which investigates hundreds or thousands of distinct liquid formulations comprising different components and/or different component ratios.

The present invention comprises a method for the determination of miscibility of a combination of two or more liquids. Generally, a miscible combination of liquids exists as one homogeneous liquid phase. A miscible mixture of liquids is one in which one or more liquids are completely soluble in another liquid. An immiscible mixture of liquids comprises at least two distinct liquid phases. Immiscibility can occur when one or more liquids in a mixture are not completely soluble in another liquid. The present invention comprises a method for the determination of miscibility based on a change in refractive index in a mixture of two or more liquids. In the case of immiscible liquids, each with an identical refractive index, the present invention may be combined with another technique to determine miscibility. The present invention provides methods for the high-throughput analysis of liquid samples.

In one aspect, the present invention provides a method for the determination of miscibility of a mixture of two or more liquids comprising:

preparing the mixture in a container;
(a) placing the container in proximity to a reference pattern;
(b) irradiating the mixture; and
(c) measuring any local deviation of a pattern characteristic of the reference pattern.

In a preferred embodiment, the present invention provides a method to determine if a combination of two or more liquids is completely miscible. The present invention also provides a method to determine if a combination of two or more liquids is partially miscible or completely immiscible.

In order to analytically determine if a combination of liquids (mixture) is miscible, the combination must be sufficiently mixed and allowed to reach equilibrium. Mixing can be accomplished, for example, via shaking, or use of a magnetic stirrer or centrifuge. The duration and intensity of mixing required for a combination of liquids is dependant upon the given combination (e.g., due to viscosity, interfacial tension), and is understood by those skilled in the art.

A container, preferably with a substantially consistent radius of curvature (e.g., test tube), should be used to hold the mixture for analysis. The term "container" includes those containers with a cylindrical shape, a semi-cylindrical shape, and a non-cylindrical shape such as, for example, a container with a planar convex shape, a planar concave shape, a bi-convex shape, a bi-concave shape, a meniscus convex shape, or a meniscus concave shape. A preferred container has a regular and/or symmetric three-dimensional geometry, however, the present invention include containers with an irregular or an asymmetric three-dimensional geometry. The container must cause a divergence or a convergence of the transmitted radiation. This convergence/divergence can be, for example, in the horizontal direction, the vertical direction, or both, or in a diagonal direction with respect to an axis of the container. (The container's major axis is defined as a line intersecting the top and bottom of the container where the top comprises an opening through which the liquid or liquids are dispensed.) Preferably, the container does not cause transmitted light to be convergent or divergent in the direction of the major axis (e.g., an upright test tube has a cylindrical shape which acts as a lens only in the horizontal direction). Such a container is considered to act as a uniaxial lens. A container with a lens that is not uniaxial (e.g., a round bottom flask, biaxial) is included in the present invention. The container must be at least partially transparent to the wavelengths of radiation used and should be placed in proximity to a reference pattern. The container can be, for example, in front of or behind the reference pattern with respect to the source of irradiation.

The reference pattern can consist of any geometric pattern with a high contrast and can consist of, for example, a two-dimensional grid, concentric circles, a set of vertical or horizontal lines with a constant or variable spacing between lines, or another regular geometric pattern. The reference pattern can consist of, for example, a high contrast design (e.g., black lines on a white background) or a high contrast pattern of fluorophores and/or phosphors. In addition, the reference pattern can consist of a transparent or a substantially transparent material with a pattern etched, drawn, or otherwise deposited onto the material surface. Detection of the pattern can be accomplished using any of a variety of spectroscopic techniques which measure, for example, elastic or inelastic scattering, reflection, transmission, fluorescence, or phosphorescence.

Upon placing the sample in proximity to the reference pattern, the sample and pattern are irradiated with infrared, visible, or ultraviolet light. The term "proximity" is defined as a distance which allows detection and imaging of the diffracted light upon interaction with both the container and the reference pattern. The light can be coherent or incoherent. In one embodiment of the present invention, the light is generated by a visible-near infrared laser (e.g., Ti:Sapphire, He—Ne, diode laser, etc.). In another embodiment, a Hg lamp is used. The light source is used to measure a local deviation of a pattern characteristic of the reference pattern through the container. The axis of irradiation is defined as a line which can be drawn between the light source, the container, and the reference pattern. In one embodiment, an image of the reference pattern is acquired. This can be accomplished in many ways known to those skilled in the art and includes, for example, a photodetector or a CCD camera. In another embodiment, an image can be acquired with the photodetector positioned, for example, in front of or behind the container and the reference pattern. In another embodiment, an image can be acquired with the photodetector positioned, for example, at an angle suitable to detect transmitted or reflected radiation from the container and the reference pattern.

Upon observation of the reference pattern through the container, the local deviation of pattern characteristics can be determined via comparison with a calibration quantity. A calibration quantity can be, for example, the distance between any two pattern characteristics of the reference pattern, or the distance between any two pattern characteristics within an acquired image. In one embodiment, an image of the reference pattern is acquired through the container. The method step of measuring a local deviation of a pattern characteristic of the reference pattern is accomplished by comparison of at least two measurements. In one embodiment, one measurement is taken of the reference pattern through a container filled with liquid and a second measurement is taken of the reference pattern itself. One measurement can be, for example, the distance between two or more pattern characteristics of the reference pattern captured as observed in an image of the pattern as viewed through the container. A second measurement can be, for example, the physical distance between two or more pattern characteristics of the reference pattern. Another measurement can be, for example, the distance between two or more pattern characteristics of the reference pattern captured as observed in an image of the pattern as viewed outside the container. Changes of pattern characteristics (e.g., magnification, demagnification), or local deviation between the top and bottom of the liquid phase(s) can indicate immiscibility of the liquids in the container. An immiscible combination of liquids can yield a local deviation in one liquid phase that is different from the local deviation of another liquid phase present in the container. In addition, an interfacial meniscus between the immiscible phases may be present. For example, a mixture of two immiscible liquids results in two liquid phases. The local deviation due to the top (less dense) liquid phase is distinct from the local deviation due to the bottom (more dense) liquid phase.

In one particular embodiment, a two-dimensional grid as a reference pattern can yield different sized rectangles when imaging an immiscible combination of liquids. In such a two-dimensional grid, a non-limiting spacing between consecutive lines can be about 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 4.0, 5.0, 6.0, 7.0, 8.0, 9.0, or 10.0 mm or more or an intermediate value. In a preferred container such as, for example, a test tube, only the vertical grid lines will appear to be modulated in the acquired image. The horizontal lines of the grid can be used, for example, to calibrate the local deviations (i.e., spacing between lines as captured by the image) of the vertical grid lines (e.g., to calculate an aspect ratio) and/or to measure distances within the image. Without being bound by theory, the change in local deviation (e.g., aspect ratio) within an acquired image is the result of a change in refractive index within the liquid sample. Such a change in refractive index is caused by the presence of two or more liquid phases, a result of an immiscible liquid combination. A miscible liquid combination is homogeneous and, therefore, will be characterized by a uniform refractive index, and will contain a local deviation of zero in pattern characteristic(s) within the liquid phase.

In another embodiment, a calibration measurement is made by dispensing a single pure liquid into a container and determining the local deviation as described above. This local deviation can be compared to the reference pattern itself or it can be compared to any portion of the reference pattern in the acquired image which was not viewed through the container. Such a measurement allows one to quantitate the magnitude of local deviation caused independently by the container and by the pure liquid. In a similar measurement, an empty container can also be investigated to determine the local deviation exclusively due to the container. These measurements can be used to quantitate the refractive index of one or more liquid phases of a combination of liquids.

In another embodiment, calibration measurements of a liquid mixture are made by determining the local deviation of each component in pure form. Each component is dispensed into a container and the local deviation is determined as described above. Such measurements allow one to quantitate the level of local deviation caused by the container and each pure liquid. These measurements can be used to quantitate the refractive index of one or more liquid phases of a combination of liquids.

In another embodiment, the refractive index of one or more components of the combination of liquids is known. In another embodiment, the refractive index of each of the components of the combination of liquids is known. This information can be used to calibrate the magnitude of local deviation captured in an image. However, knowledge of the refractive index of any pure component or of any combination of liquids is not required for the present invention. In another embodiment, the refractive index of a component of the liquid mixture is not known.

In another embodiment, a calibration of each component of the liquid combination can be made as to the level of local deviation caused by each component alone. Such information can be used to determine, for example, complete miscibility, partial miscibility, or complete immiscibility of a component combination.

In another embodiment, the local deviation is determined for a pure liquid in a container. Then, a second liquid is added to the container. In the case of an immiscible liquid combination, for example, the second liquid dispensed may remain on top of the first liquid or the second liquid may displace the first liquid at the bottom of the container. The combination of liquids is appropriately mixed and allowed to reach equilibrium. The local deviation is again determined throughout the liquid phase in the container to determine if the liquids are miscible. In another embodiment, a third liquid is added to the mixture. In another embodiment, a fourth or subsequent components are added to the mixture.

In another embodiment, the local deviation is measured following transmission of radiation through first, the container, followed by the reference pattern. In another embodiment, the local deviation is measured following transmission of radiation through first, the reference pattern, followed by the container.

The present invention is suitable for a diverse array of liquid excipients. For example, aqueous, non-aqueous, and viscous liquids (e.g., solvents, enhancers, solubilizers, etc.) are included via the terms "liquid excipients" or "liquids," according to the present invention.

In another embodiment, combinations of liquid excipients comprising one or more solute molecules in solution (e.g., an active pharmaceutical ingredient (API), solid excipient) are also included in the present invention.

In another embodiment, the miscibility of two or more liquids can be determined via a laser displacement method. Specifically, this embodiment comprises a light beam passing through a transparent container, wherein the container further comprises a combination of two or more liquids. The beam is directed through the container and towards a photodetector. The method comprises moving the beam relative to the container in a vertical direction. In one embodiment, the beam is scanned vertically in an upward or downward direction through the entire portion of the container where liquid is present. Optionally, the detector is also moved in concert with the light beam so as to remain in alignment. In another embodiment, the container is mechanically moved in an upward or downward vertical direction to facilitate transmission of the beam throughout the entire liquid-containing region. Such an apparatus and method can be used to measure variations in beam intensity upon relative vertical motion of the beam and container caused by an interfacial region (e.g., meniscus). The variations in beam intensity are due to beam displacement caused by the transmission of light through a region of discontinuity within the liquid sample. A discontinuity within the liquid sample can be, for example, an interfacial region or a meniscus, due to the immiscibility of two or more liquids within the container.

In another embodiment, a method for the determination of miscibility of a mixture of two or more liquids is provided, comprising:
(a) preparing the mixture in a container;
(b) placing the container between a laser source and a photodetector;
(c) scanning the mixture in a vertical direction; and
(d) measuring any variation in beam intensity.

The angle of incidence between the container and the light beam can be about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or about 175 degrees, or any intermediate angle. In one embodiment, the angle of incidence between the container and the light beam is between about 45 and 85 degrees or between about 95 and 135 degrees. In another embodiment, the angle of incidence between the container and the light beam is between about 60 and 85 degrees or between about 95 and 120 degrees. For example, about 60, 65, 70, 75, or about 80 degrees. The angle of incidence is defined, herein, as the angle between the bottom of the container and the light beam.

The wavelength(s) of light used may be, for example, in the ultraviolet, visible, or infrared regions of the electromagnetic spectrum. The light may be coherent or incoherent. Preferably, the wavelength(s) of light used in the determination are not significantly absorbed by the liquid mixture.

Several embodiments of the present invention can be used to analyze liquid samples in parallel. Two, three, four, eight, or more liquid samples can be probed simultaneously in order to enable the analysis of larger numbers of liquid samples. In one embodiment, such a parallel analysis of samples can be accomplished via splitting the light beam into two, three, four, or eight or more beams. In such an embodiment, each beam can be directed to an independent photodetector.

In another embodiment, the light beam is of an appropriate size (either by expansion of the light beam or by virtue of an appropriate incoherent light source, e.g., mercury lamp) so as to allow simultaneous interrogation of the entire liquid sample. In another embodiment, the photodetector is capable of measuring the intensity of the transmitted light from the entire container simultaneously (e.g., CCD camera). Such embodiments can remove the necessity of scanning the liquid sample.

In another embodiment, the photodetector (e.g., photomultiplier tube, CCD camera, etc.) of the present invention is connected to a computer and, optionally, the data collection may be controlled by one or more algorithms. In another embodiment, the light source (e.g., laser, shutter, etc.) of the present invention is connected to a computer and may, optionally, be controlled by one or more algorithms. In another embodiment, both the photodetector and the light source are connected to a computer and may, optionally, be controlled by one or more algorithms.

In another embodiment, the container is positioned via linear actuators before analysis of the sample. Optionally, the linear actuators are controlled by a computer. In another embodiment, the present invention provides a method for the high-throughput analysis of at least about 10, 15, 20, 25, 80, 85, 90, 95, 100, 200, 300, 400, 500, 600, 700, 800, 900, 1000, 1500, 2000, 2500, 3000, 3500, 4000, 4500, or 5000 samples.

Although the present invention has been described in considerable detail with reference to certain embodiments, other embodiments are possible. Therefore, the spirit and scope of the appended claims should not be limited to the description of the embodiments contained herein. Modifications and variations of the invention described herein will be obvious to those skilled in the art from the foregoing detailed description and such modifications and variations are intended to come within the scope of the appended claims.

What is claimed is:

1. A method for the determination of miscibility of a mixture of two or more liquids comprising:
    (a) preparing said mixture in a container, wherein the shape of said container causes convergence or divergence of transmitted radiation;
    (b) placing said container in proximity to a reference pattern;
    (c) irradiating said mixture; and
    (d) measuring any local deviation of a pattern characteristic of said reference pattern;
   wherein said reference pattern is substantially transparent and a substrate for said reference pattern is opaque.

2. A method for the determination of miscibility of a mixture of two or more liquids comprising:
    (a) preparing said mixture in a container, wherein the shape of said container causes convergence or divergence of transmitted radiation;
    (b) placing said container in proximity to a reference pattern;
    (c) irradiating said mixture; and
    (d) measuring any local deviation of a pattern characteristic of said reference pattern;
   wherein said local deviation is measured following transmission of radiation through said container followed by said reference pattern.

3. A method for the determination of miscibility of a mixture of two or more liquids comprising:
    (a) preparing said mixture in a container, wherein the shape of said container causes convergence or divergence of transmitted radiation;
    (b) placing said container in proximity to a reference pattern;
    (c) irradiating said mixture; and
    (d) measuring any local deviation of a pattern characteristic of said reference pattern;
   wherein said local deviation is captured in an image, further wherein said image is acquired using a photodetector, further wherein said photodetector is positioned such that it detects radiation from a source of irradiation after it has passed through said container and reference pattern, and further wherein said radiation is transmitted by said container followed by said reference pattern.

4. A method for the determination of miscibility of a mixture of two or more liquids comprising:
    (a) preparing said mixture in a container, wherein the shape of said container causes convergence or divergence of transmitted radiation;
    (b) placing said container in proximity to a reference pattern;
    (c) irradiating said mixture; and
    (d) measuring any local deviation of a pattern characteristic of said reference pattern;
   wherein said local deviation is captured in an image, further wherein said image is acquired using a photodetector, further wherein said photodetector is positioned such that it detects radiation from a source of irradiation after it has passed through said container and reference pattern, and further wherein said radiation is reflected after passing through said container and reference pattern.

5. A method for the determination of miscibility of a mixture of two or more liquids comprising:
    (a) preparing said mixture in a container, wherein the shape of said container causes convergence or divergence of transmitted radiation;
    (b) placing said container in proximity to a reference pattern;
    (c) irradiating said mixture; and
    (d) measuring any local deviation of a pattern characteristic of said reference pattern;
   wherein said local deviation is captured in an image, further wherein said image is acquired using a photodetector, further wherein said photodetector is positioned such that it detects radiation from a source of irradiation after it has passed through said container and reference pattern, and further wherein said radiation is reflected after transmission through said reference pattern followed by said container.

6. A method for the determination of miscibility of a mixture of two or more liquids comprising:
    (a) preparing said mixture in a container, wherein the shape of said container causes convergence or divergence of transmitted radiation;
    (b) placing said container in proximity to a reference pattern;
    (c) irradiating said mixture; and
    (d) measuring any local deviation of a pattern characteristic of said reference pattern;
   wherein said local deviation is captured in an image, further wherein said image is acquired using a photodetector, further wherein said photodetector is positioned such that it detects radiation from a source of irradiation after it has passed through said container and reference pattern, and further wherein said radiation is reflected after transmission through said container followed by said reference pattern.

7. A method for the determination of miscibility of a mixture of two or more liquids comprising:
    (a) preparing said mixture in a container, wherein the shape of said container causes convergence or divergence of transmitted radiation;
    (b) placing said container in proximity to a reference pattern;
    (c) irradiating said mixture; and
    (d) measuring any local deviation of a pattern characteristic of said reference pattern;
   wherein said reference pattern is opaque and a substrate for said reference pattern is substantially transparent.

8. A method for the determination of miscibility of a mixture of two or more liquids comprising:

(a) preparing said mixture in a container, wherein the shape of said container causes convergence or divergence of transmitted radiation;
(b) placing said container in proximity to a reference pattern;
(c) irradiating said mixture; and
(d) measuring any local deviation of a pattern characteristic of said reference pattern;

wherein said reference pattern is reflective and is mounted on a nonreflective or less reflective substrate.

9. A method for the determination of miscibility of a mixture of two or more liquids comprising:

(a) preparing said mixture in a container, wherein the shape of said container causes convergence or divergence of transmitted radiation;
(b) placing said container in proximity to a reference pattern;
(c) irradiating said mixture; and
(d) measuring any local deviation of a pattern characteristic of said reference pattern;

wherein said reference pattern is nonreflective and is mounted on a reflective or more reflective substrate.

* * * * *